(12) United States Patent
Perschbacher et al.

(10) Patent No.: US 10,350,419 B2
(45) Date of Patent: Jul. 16, 2019

(54) SUPRAVENTRICULAR TACHY SENSING VECTOR

(71) Applicant: Cardiac Pacemakers, Inc., St. Paul, MN (US)

(72) Inventors: David L. Perschbacher, Coon Rapids, MN (US); James O. Gilkerson, Stillwater, MN (US); Ron A. Balczewski, Bloomington, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 295 days.

(21) Appl. No.: 15/265,674

(22) Filed: Sep. 14, 2016

(65) Prior Publication Data

US 2017/0001020 A1    Jan. 5, 2017

Related U.S. Application Data

(63) Continuation of application No. 12/277,101, filed on Nov. 24, 2008, now abandoned.

(60) Provisional application No. 61/007,635, filed on Dec. 13, 2007.

(51) Int. Cl.
*A61B 5/04* (2006.01)
*A61N 1/362* (2006.01)
*A61N 1/365* (2006.01)
*A61N 1/39* (2006.01)
(Continued)

(52) U.S. Cl.
CPC ........ *A61N 1/3702* (2013.01); *A61B 5/04011* (2013.01); *A61B 5/0464* (2013.01); *A61N 1/3622* (2013.01); *A61N 1/36592* (2013.01); *A61N 1/3925* (2013.01); *A61N 1/3962* (2013.01)

(58) Field of Classification Search
CPC .............. A61B 5/04011; A61N 1/3622; A61N 1/36592; A61N 1/3962
See application file for complete search history.

(56) References Cited

U.S. PATENT DOCUMENTS

| 3,857,399 A | 12/1974 | Zacouto |
| 4,030,510 A | 6/1977 | Bowers |
| 4,059,116 A | 11/1977 | Adams |

(Continued)

FOREIGN PATENT DOCUMENTS

| EP | 0033418 A1 | 8/1981 |
| EP | 0360412 A1 | 3/1990 |

(Continued)

OTHER PUBLICATIONS

"", Metrix Model 3020 Implantable Atrial Defibrillator, Physician's Manual, InControl, Inc., Redmond, WA, (1998), pp. 4-24-4-27.

(Continued)

*Primary Examiner* — William J Levicky
(74) *Attorney, Agent, or Firm* — Schwegman Lundberg & Woessner, P.A.

(57) ABSTRACT

A system includes a pulse generator including a can electrode and a lead couplable to the pulse generator, the lead including a distal coil electrode and a proximal coil electrode, wherein both of the coil electrodes are electrically uncoupled from the can electrode such that a unipolar sensing vector is provided between at least one of the coil electrodes and the can electrode.

8 Claims, 1 Drawing Sheet

(51) Int. Cl.
*A61N 1/37* (2006.01)
*A61B 5/0464* (2006.01)

(56) References Cited

U.S. PATENT DOCUMENTS

| | | |
|---|---|---|
| 4,163,451 A | 8/1979 | Lesnick et al. |
| 4,208,008 A | 6/1980 | Smith |
| RE30,387 E | 8/1980 | Denniston, III et al. |
| 4,432,360 A | 2/1984 | Mumford et al. |
| 4,485,818 A | 12/1984 | Leckrone et al. |
| 4,503,857 A | 3/1985 | Boute et al. |
| 4,556,063 A | 12/1985 | Thompson et al. |
| 4,562,841 A | 1/1986 | Brockway et al. |
| 4,596,255 A | 6/1986 | Snell et al. |
| 4,791,936 A | 12/1988 | Snell et al. |
| 4,809,697 A | 3/1989 | Causey, III et al. |
| 4,830,006 A | 5/1989 | Haluska et al. |
| 4,856,523 A | 8/1989 | Sholder et al. |
| 4,860,749 A | 8/1989 | Lehmann |
| 4,869,252 A | 9/1989 | Gilli |
| 4,890,617 A | 1/1990 | Markowitz et al. |
| 4,905,697 A | 3/1990 | Heggs et al. |
| 4,917,115 A | 4/1990 | Flammang et al. |
| 4,920,965 A | 5/1990 | Funke et al. |
| 4,928,688 A | 5/1990 | Mower |
| 4,932,406 A | 6/1990 | Berkovits |
| 4,940,054 A | 7/1990 | Grevis et al. |
| 4,941,471 A | 7/1990 | Mehra |
| 4,944,298 A | 7/1990 | Sholder |
| 4,944,928 A | 7/1990 | Grill et al. |
| 4,945,909 A | 8/1990 | Fearnot et al. |
| 4,972,834 A | 11/1990 | Begemann et al. |
| 4,998,974 A | 3/1991 | Aker |
| 5,012,814 A | 5/1991 | Mills et al. |
| 5,042,480 A | 8/1991 | Hedin et al. |
| 5,077,667 A | 12/1991 | Brown et al. |
| 5,085,215 A | 2/1992 | Nappholz et al. |
| 5,101,824 A | 4/1992 | Lekholm |
| 5,107,850 A | 4/1992 | Olive |
| 5,127,404 A | 7/1992 | Wyborny et al. |
| 5,129,394 A | 7/1992 | Mehra |
| 5,133,350 A | 7/1992 | Duffin |
| 5,139,020 A | 8/1992 | Koestner et al. |
| 5,144,949 A | 9/1992 | Olson |
| 5,156,147 A | 10/1992 | Warren et al. |
| 5,156,154 A | 10/1992 | Valenta, Jr. et al. |
| 5,176,136 A | 1/1993 | Giele |
| 5,179,949 A | 1/1993 | Chirife |
| 5,183,040 A | 2/1993 | Nappholz et al. |
| 5,184,614 A | 2/1993 | Collins et al. |
| 5,188,106 A | 2/1993 | Nappholz et al. |
| 5,193,535 A | 3/1993 | Bardy et al. |
| 5,193,550 A | 3/1993 | Duffin |
| 5,197,467 A | 3/1993 | Steinhaus et al. |
| 5,207,219 A | 5/1993 | Adams et al. |
| 5,226,415 A | 7/1993 | Girodo et al. |
| 5,282,836 A | 2/1994 | Kreyenhagen et al. |
| 5,284,491 A | 2/1994 | Sutton et al. |
| 5,292,339 A | 3/1994 | Stephens et al. |
| 5,292,341 A | 3/1994 | Snell |
| 5,311,874 A | 5/1994 | Baumann et al. |
| 5,312,452 A | 5/1994 | Salo |
| 5,331,966 A | 7/1994 | Bennett et al. |
| 5,334,220 A | 8/1994 | Sholder |
| 5,340,361 A | 8/1994 | Sholder |
| 5,350,409 A | 9/1994 | Stoop et al. |
| 5,356,425 A | 10/1994 | Bardy et al. |
| 5,360,437 A | 11/1994 | Thompson |
| 5,365,932 A | 11/1994 | Greenhut |
| 5,372,607 A | 12/1994 | Stone et al. |
| 5,379,776 A | 1/1995 | Murphy et al. |
| 5,383,910 A | 1/1995 | den Dulk |
| 5,387,229 A | 2/1995 | Poore |
| 5,391,189 A | 2/1995 | van Krieken et al. |
| 5,395,373 A | 3/1995 | Ayers |
| 5,395,397 A | 3/1995 | Lindgren et al. |
| 5,400,796 A | 3/1995 | Wecke |
| 5,411,524 A | 5/1995 | Rahul |
| 5,411,531 A | 5/1995 | Hill et al. |
| 5,417,714 A | 5/1995 | Levine et al. |
| 5,423,869 A | 6/1995 | Poore et al. |
| 5,431,691 A | 7/1995 | Snell et al. |
| 5,437,285 A | 8/1995 | Verrier et al. |
| 5,462,060 A | 10/1995 | Jacobson et al. |
| 5,474,574 A | 12/1995 | Payne et al. |
| 5,480,413 A | 1/1996 | Greenhut et al. |
| 5,486,198 A | 1/1996 | Ayers et al. |
| 5,487,752 A | 1/1996 | Salo et al. |
| 5,507,782 A | 4/1996 | Kieval et al. |
| 5,507,784 A | 4/1996 | Hill et al. |
| 5,514,163 A | 5/1996 | Markowitz et al. |
| 5,522,850 A | 6/1996 | Yomtov et al. |
| 5,522,859 A | 6/1996 | Stroebel et al. |
| 5,523,942 A | 6/1996 | Tyler et al. |
| 5,527,347 A | 6/1996 | Shelton et al. |
| 5,534,016 A | 7/1996 | Boute |
| 5,540,232 A | 7/1996 | Laney et al. |
| 5,540,727 A | 7/1996 | Tockman et al. |
| 5,545,182 A | 8/1996 | Stotts et al. |
| 5,545,186 A | 8/1996 | Olson et al. |
| 5,549,649 A | 8/1996 | Florio et al. |
| 5,549,654 A | 8/1996 | Powell |
| 5,554,174 A | 9/1996 | Causey, III |
| 5,560,369 A | 10/1996 | McClure et al. |
| 5,560,370 A | 10/1996 | Verrier et al. |
| 5,584,864 A | 12/1996 | White |
| 5,584,867 A | 12/1996 | Limousin et al. |
| 5,591,215 A | 1/1997 | Greenhut et al. |
| 5,605,159 A | 2/1997 | Smith et al. |
| 5,607,460 A | 3/1997 | Kroll et al. |
| 5,613,495 A | 3/1997 | Mills et al. |
| 5,620,471 A | 4/1997 | Duncan |
| 5,620,473 A | 4/1997 | Poore |
| 5,622,178 A | 4/1997 | Gilham |
| 5,626,620 A | 5/1997 | Kieval et al. |
| 5,626,622 A | 5/1997 | Cooper |
| 5,626,623 A | 5/1997 | Kieval et al. |
| 5,632,267 A | 5/1997 | Hognelid et al. |
| 5,674,250 A | 10/1997 | de Coriolis et al. |
| 5,674,251 A | 10/1997 | Combs et al. |
| 5,674,255 A | 10/1997 | Walmsley et al. |
| 5,676,153 A | 10/1997 | Smith et al. |
| 5,683,429 A | 11/1997 | Mehra |
| 5,690,686 A | 11/1997 | Min et al. |
| 5,690,689 A | 11/1997 | Sholder |
| 5,700,283 A | 12/1997 | Salo |
| 5,702,424 A | 12/1997 | Legay et al. |
| 5,713,928 A | 2/1998 | Bonnet et al. |
| 5,713,929 A | 2/1998 | Hess et al. |
| 5,713,930 A | 2/1998 | van der Veen et al. |
| 5,713,932 A | 2/1998 | Gillberg et al. |
| 5,716,382 A | 2/1998 | Snell |
| 5,716,383 A | 2/1998 | Kieval et al. |
| 5,716,384 A | 2/1998 | Snell |
| 5,718,235 A | 2/1998 | Golosarsky et al. |
| 5,724,985 A | 3/1998 | Snell et al. |
| 5,725,559 A | 3/1998 | Alt et al. |
| 5,725,561 A | 3/1998 | Stroebel et al. |
| 5,730,141 A | 3/1998 | Fain et al. |
| 5,730,142 A | 3/1998 | Sun et al. |
| 5,738,096 A | 4/1998 | Ben-Haim |
| 5,741,304 A | 4/1998 | Patwardhan et al. |
| 5,741,308 A | 4/1998 | Sholder |
| 5,749,901 A | 5/1998 | Bush et al. |
| 5,749,906 A | 5/1998 | Kieval et al. |
| 5,755,736 A | 5/1998 | Gillberg et al. |
| 5,755,737 A | 5/1998 | Prieve et al. |
| 5,755,739 A | 5/1998 | Sun et al. |
| 5,755,740 A | 5/1998 | Nappholz |
| 5,759,196 A | 6/1998 | Hess et al. |
| 5,776,164 A | 7/1998 | Ripart |
| 5,776,167 A | 7/1998 | Levine et al. |
| 5,782,887 A | 7/1998 | van Krieken et al. |
| 5,782,888 A | 7/1998 | Sun et al. |

(56) References Cited

U.S. PATENT DOCUMENTS

| | | |
|---|---|---|
| 5,788,717 A | 8/1998 | Mann et al. |
| 5,792,193 A | 8/1998 | Stoop |
| 5,792,200 A | 8/1998 | Brewer |
| 5,800,464 A | 9/1998 | Kieval |
| 5,800,471 A | 9/1998 | Baumann |
| 5,814,077 A | 9/1998 | Sholder et al. |
| 5,814,081 A | 9/1998 | Ayers et al. |
| 5,814,085 A | 9/1998 | Hill |
| 5,836,975 A | 11/1998 | DeGroot |
| 5,836,987 A | 11/1998 | Baumann et al. |
| 5,840,079 A | 11/1998 | Warman et al. |
| 5,842,997 A | 12/1998 | Verrier et al. |
| 5,846,263 A | 12/1998 | Peterson et al. |
| 5,853,426 A | 12/1998 | Shieh |
| 5,855,593 A | 1/1999 | Olson et al. |
| 5,861,007 A | 1/1999 | Hess et al. |
| 5,865,838 A | 2/1999 | Obel et al. |
| 5,871,507 A | 2/1999 | Obel et al. |
| 5,873,895 A | 2/1999 | Sholder et al. |
| 5,873,897 A | 2/1999 | Armstrong et al. |
| 5,876,422 A | 3/1999 | Van Groeningen |
| 5,891,178 A | 4/1999 | Mann et al. |
| 5,893,882 A | 4/1999 | Peterson et al. |
| 5,897,575 A | 4/1999 | Wickham |
| 5,902,324 A | 5/1999 | Thompson et al. |
| 5,928,271 A | 7/1999 | Hess et al. |
| 5,931,856 A | 8/1999 | Bouhour et al. |
| 5,931,857 A | 8/1999 | Prieve et al. |
| 5,935,081 A | 8/1999 | Kadhiresan |
| 5,944,744 A | 8/1999 | Paul et al. |
| 5,951,592 A | 9/1999 | Murphy |
| 5,968,079 A | 10/1999 | Warman et al. |
| 5,968,081 A | 10/1999 | Levine |
| 5,974,341 A | 10/1999 | Er et al. |
| 5,978,707 A | 11/1999 | Krig et al. |
| 5,978,710 A | 11/1999 | Prutchi et al. |
| 5,983,138 A | 11/1999 | Kramer |
| 5,987,354 A | 11/1999 | Cooper et al. |
| 5,987,356 A | 11/1999 | DeGroot |
| 5,991,656 A | 11/1999 | Olson et al. |
| 5,991,657 A | 11/1999 | Kim |
| 5,991,662 A | 11/1999 | Kim et al. |
| 5,999,850 A | 12/1999 | Dawson et al. |
| 5,999,854 A | 12/1999 | Deno et al. |
| 6,026,320 A | 2/2000 | Carlson et al. |
| 6,041,251 A | 3/2000 | Kim et al. |
| 6,044,298 A | 3/2000 | Salo et al. |
| 6,047,210 A | 4/2000 | Kim et al. |
| 6,049,735 A | 4/2000 | Hartley et al. |
| 6,052,617 A | 4/2000 | Kim |
| 6,052,620 A | 4/2000 | Gillberg et al. |
| 6,058,328 A | 5/2000 | Levine et al. |
| 6,070,101 A | 5/2000 | Struble et al. |
| 6,081,745 A | 6/2000 | Mehra |
| 6,081,746 A | 6/2000 | Pendekanti et al. |
| 6,081,747 A | 6/2000 | Levine et al. |
| 6,081,748 A | 6/2000 | Struble et al. |
| RE36,765 E | 7/2000 | Mehra |
| 6,085,116 A | 7/2000 | Pendekanti et al. |
| 6,088,618 A | 7/2000 | Kerver |
| 6,091,988 A | 7/2000 | Warman et al. |
| 6,096,064 A | 8/2000 | Routh |
| 6,122,545 A | 9/2000 | Struble et al. |
| 6,128,529 A | 10/2000 | Elser |
| 6,129,745 A | 10/2000 | Sun et al. |
| 6,134,469 A | 10/2000 | Wietholt |
| 6,151,524 A | 11/2000 | Krig et al. |
| 6,219,579 B1 | 4/2001 | Bakels et al. |
| 6,223,072 B1 | 4/2001 | Mika et al. |
| 6,223,079 B1 | 4/2001 | Bakels et al. |
| 6,223,082 B1 | 4/2001 | Bakels et al. |
| 6,238,420 B1 | 5/2001 | Bakels et al. |
| 6,246,909 B1 | 6/2001 | Ekwall |
| 6,249,699 B1 | 6/2001 | Kim |
| 6,256,534 B1 | 7/2001 | Dahl |
| 6,263,242 B1 | 7/2001 | Mika et al. |
| 6,266,554 B1 | 7/2001 | Hsu et al. |
| 6,272,380 B1 | 8/2001 | Warman et al. |
| 6,275,734 B1 | 8/2001 | McClure et al. |
| 6,280,391 B1 | 8/2001 | Olson et al. |
| 6,285,907 B1 | 9/2001 | Kramer et al. |
| 6,292,693 B1 | 9/2001 | Darvish et al. |
| 6,317,632 B1 | 11/2001 | Krig et al. |
| 6,324,425 B1 * | 11/2001 | Blow .................. A61N 1/3627 607/13 |
| 6,351,669 B1 | 2/2002 | Hartley et al. |
| 6,353,759 B1 | 3/2002 | Hartley et al. |
| 6,353,761 B1 | 5/2002 | Conley et al. |
| 6,408,209 B1 | 6/2002 | Bouhour et al. |
| 6,411,847 B1 | 6/2002 | Mower |
| 6,411,848 B2 | 6/2002 | Kramer et al. |
| 6,421,564 B1 | 7/2002 | Yerich et al. |
| 6,424,865 B1 | 7/2002 | Ding |
| 6,430,438 B1 | 8/2002 | Chen et al. |
| 6,430,439 B1 | 8/2002 | Wentkowski et al. |
| 6,434,424 B1 | 8/2002 | Igel et al. |
| 6,438,410 B2 | 8/2002 | Hsu et al. |
| 6,438,421 B1 | 8/2002 | Stahmann et al. |
| 6,501,987 B1 | 12/2002 | Lovett et al. |
| 6,501,988 B2 | 12/2002 | Kramer et al. |
| 6,512,951 B1 | 1/2003 | Marcovecchio et al. |
| 6,522,925 B1 | 2/2003 | Gilkerson et al. |
| RE38,119 E | 5/2003 | Mower |
| 6,687,541 B2 | 2/2004 | Marcovecchio et al. |
| 6,760,615 B2 | 7/2004 | Ferek-Petric |
| 6,763,267 B2 | 7/2004 | Ding |
| 6,847,842 B1 | 1/2005 | Rodenhiser et al. |
| 6,957,100 B2 | 10/2005 | Vanderlinde et al. |
| 7,013,176 B2 | 3/2006 | Ding et al. |
| 7,069,077 B2 | 6/2006 | Lovett et al. |
| 7,120,490 B2 | 10/2006 | Chen et al. |
| 7,123,960 B2 | 10/2006 | Ding et al. |
| 7,142,915 B2 | 11/2006 | Kramer et al. |
| 7,142,918 B2 | 11/2006 | Stahmann et al. |
| 7,184,834 B1 | 2/2007 | Levine |
| 7,203,540 B2 | 4/2007 | Ding et al. |
| 7,266,411 B1 | 9/2007 | Paris et al. |
| 7,283,872 B2 | 10/2007 | Boute et al. |
| 7,308,310 B1 | 12/2007 | Levine et al. |
| 7,460,908 B2 | 12/2008 | Krig et al. |
| 2002/0062139 A1 | 5/2002 | Ding |
| 2002/0082509 A1 | 6/2002 | Vanderlinde et al. |
| 2002/0082660 A1 | 6/2002 | Stahmann et al. |
| 2002/0087198 A1 | 7/2002 | Kramer et al. |
| 2002/0091415 A1 | 7/2002 | Lovett et al. |
| 2002/0120298 A1 | 8/2002 | Kramer et al. |
| 2003/0004551 A1 | 1/2003 | Chen et al. |
| 2003/0069610 A1 | 4/2003 | Kramer et al. |
| 2003/0078630 A1 | 4/2003 | Lovett et al. |
| 2003/0083587 A1 | 5/2003 | Ferek-Petric |
| 2003/0105491 A1 | 6/2003 | Gilkerson et al. |
| 2003/0204214 A1 | 10/2003 | Ferek-Patric |
| 2003/0233131 A1 | 12/2003 | Kramer et al. |
| 2004/0010295 A1 | 1/2004 | Kramer et al. |
| 2004/0077963 A1 | 4/2004 | Perschbacher et al. |
| 2004/0172076 A1 | 9/2004 | Stahmann et al. |
| 2004/0215249 A1 | 10/2004 | Corbucci |
| 2004/0215259 A1 | 10/2004 | Krig et al. |
| 2004/0243188 A1 | 12/2004 | Vanderlinde et al. |
| 2004/0254613 A1 * | 12/2004 | Ostroff ................ A61N 1/3956 607/5 |
| 2005/0038480 A1 | 2/2005 | Ding |
| 2005/0192506 A1 * | 9/2005 | Kim ..................... A61B 5/0402 600/510 |
| 2005/0283196 A1 | 12/2005 | Bocek et al. |
| 2005/0288719 A1 | 12/2005 | Zhang et al. |
| 2006/0111747 A1 | 5/2006 | Cazares et al. |
| 2006/0116594 A1 | 6/2006 | Zhang et al. |
| 2006/0219252 A1 | 6/2006 | Bardy et al. |
| 2006/0167508 A1 | 7/2006 | Boute et al. |
| 2006/0195150 A1 | 8/2006 | Lovett |
| 2006/0195151 A1 | 8/2006 | Vanderlinde et al. |

(56) References Cited

U.S. PATENT DOCUMENTS

| | | |
|---|---|---|
| 2009/0149904 A1 | 6/2009 | Perschbacher et al. |
| 2009/0149907 A1 | 6/2009 | Perschbacher et al. |
| 2009/0157133 A1 | 6/2009 | Perschbacher et al. |

FOREIGN PATENT DOCUMENTS

| | | |
|---|---|---|
| EP | 0401962 A2 | 12/1990 |
| EP | 0597459 A2 | 5/1994 |
| EP | 0617980 A2 | 10/1994 |
| EP | 0674917 A2 | 10/1995 |
| EP | 0748638 A2 | 12/1996 |
| JP | 2007513708 A | 5/2007 |
| JP | 2007517549 A | 7/2007 |
| WO | WO-9302746 A1 | 2/1993 |
| WO | WO-9509029 A2 | 4/1995 |
| WO | WO-9711745 A1 | 4/1997 |
| WO | WO-9739798 A1 | 10/1997 |
| WO | WO-9848891 A1 | 11/1998 |
| WO | WO-0004950 A2 | 2/2000 |
| WO | WO-0038782 A1 | 7/2000 |
| WO | WO-0047277 A1 | 8/2000 |
| WO | WO-0071200 A1 | 11/2000 |
| WO | WO-0071202 A1 | 11/2000 |
| WO | WO-0071203 A1 | 11/2000 |
| WO | WO-02045797 A2 | 6/2002 |
| WO | WO-2005058412 A2 | 6/2005 |
| WO | WO-09075725 A1 | 6/2009 |
| WO | WO-09075749 A1 | 6/2009 |

OTHER PUBLICATIONS

"U.S. Appl. No. 09/316,588, Non Final Office Action dated Nov. 21, 2000", 4 pgs.

"U.S. Appl. No. 09/316,588, Notice of Allowance dated Mar. 19, 2001", 6 pgs.

"U.S. Appl. No. 09/316,588, Response filed Feb. 21, 2001 to Non Final Office Action dated Nov. 21, 2000", 10 pgs.

"U.S. Appl. No. 09/837,019, Non Final Office Action dated Aug. 1, 2001", 5 pgs.

"U.S. Appl. No. 09/837,019, Notice of Allowance dated Feb. 8, 2002", 3 pgs.

"U.S. Appl. No. 10/852,602, Corrected Notice of Allowance dated Aug. 4, 2008", 4 pgs.

"U.S. Appl. No. 10/852,602, Notice Of Allowance dated Jul. 11, 2007", 9 pgs.

"U.S. Appl. No. 11/380,148, Restriction Requirement dated Oct. 29, 2008", 7 pgs.

"U.S. Appl. No. 12/277,101, Appeal Brief filed Mar. 26, 2014", 11 pgs.

"U.S. Appl. No. 12/277,101, Appeal Decision mailed Jul. 15, 2016", 6 pgs.

"U.S. Appl. No. 12/277,101, Final Office Action dated Aug. 15, 2013", 8 pgs.

"U.S. Appl. No. 12/277,101, Final Office Action dated Oct. 1, 2012", 7 pgs.

"U.S. Appl. No. 12/277,101, Final Office Action dated Nov. 8, 2011", 10 pgs.

"U.S. Appl. No. 12/277,101, Non Final Office Action dated Mar. 7, 2013", 8 pgs.

"U.S. Appl. No. 12/277,101, Non Final Office Action dated Mar. 28, 2012", 7 pgs.

"U.S. Appl. No. 12/277,101, Non Final Office Action dated Jun. 29, 2011", 9 pgs.

"U.S. Appl. No. 12/277,101, Response filed Feb. 8, 2012 to Final Office Action dated Nov. 8, 2011", 8 pgs.

"U.S. Appl. No. 12/277,101, Response filed Mar. 1, 2013 to Final Office Action dated Oct. 1, 2012", 8 pgs.

"U.S. Appl. No. 12/277,101, Response filed Jun. 7, 2013 to Non Final Office Action dated Mar. 7, 2013", 7 pgs.

"U.S. Appl. No. 12/277,101, Response filed Aug. 8, 2012 to Non Final Office Action dated Mar. 28, 2012", 11 pgs.

"U.S. Appl. No. 12/277,101, Response filed Oct. 27, 2011 to Non Final Office Action dated Jun. 29, 2011", 8 pgs.

"U.S. Appl. No. 12/327,567, Non-Final Office Action dated Sep. 22, 2010", 8 pgs.

"French CNH Equipment Approvals", Clinica, 417, p. 9, (Sep. 5, 1990), 3 pgs.

"International Application Serial No. PCT/US2008/013069, International Search Report dated Mar. 27, 2009", 5 pgs.

"International Application Serial No. PCT/US2008/013305, Search Report dated Mar. 18, 2009", 8 pgs.

"International Application Serial No. PCT/US2008/013305, Written Opinion dated Mar. 18, 2009", 8 pgs.

"International Application Serial No. PCT/US2008/013960, Written Opinion dated Mar. 27, 2009", 8 pgs.

"Japanease Application Serial No. 2010-537922, Office Action dated Jul. 3, 2012", With English Translation, 7 pgs.

"Japanese Application Serial No. 2010-537922, Office Action dated Dec. 18, 2012", With English Translation, 7 pgs.

"Japanese Application Serial No. 2010-537922, Response filed Sep. 26, 2012 to Office Action dated Jul. 3, 2012", With English Claims, 7 pgs.

"Pacemaker System Guide", (c) 2001 Guidant Corporation, 240 pgs.

"Pacemaker System Guide for Pulsar Max II; Mulitprogrammable Pacemakers", Product brochure published by Guidant Corporation, (Apr. 18, 1999), pp. 6-48 and 6-49.

"Pacemaker System Guide for Pulsar Max II; Multiprogrammable Pacemakers", Product brochure published by Guidant Corporation, (Apr. 18, 1999), p. 6-39-6-51.

"Rate-Adaptive Devices Impact Pacemaker Market", Clinica, 467, p. 16, (Sep. 11, 1991), 6 pgs.

"Vitatron Medical Harmony Automatic Dual Chamber Pacemaker Product Information and Programming Guide", Viatron Medical, 22 p., (Date Unknown), Harmony Dual Chamber mentioned in publication Clinica, 467, p. 16, Sep. 11, 1991, "Rate Devices Impact Pacemaker Market", also mentioned in Clinica, 417, p. 9, Sep. 5, 1990 "French CNH Equipment Approvals"., Product Brochure published by Vitatron Medical, 22 pgs.

Ayers, Gregory M., et al., "Ventricular Proarrhythmic Effects of Ventricular Cycle Length and Shock Strength in a Sheep Model of Transvenous Atrial Defibrillation", Circulation, 89 (1), (Jan. 1994), 413-422.

Blommaert, D., et al., "Effective Prevention of Atrial Fibrillation by Continuous Atrial Overdrive Pacing After Coronary Artery Bypass Surgery", JACC, vol. 35, No. 6, (May 2000), 1411-1415 pgs.

Buhr, T. A., et al., "Novel Pacemaker Algorithm Diminishes Short-Coupled Ventricular Beats In Atrial Fibrillation", Pacing and Clinical Electrophysiology, vol. 24, Part II, (Abstract Only), (Apr. 2001), 729 pgs.

Campbell, R. M., et al., "Atrial Overdrive Pacing for Conversion of Atrial Flutter in Children", Pediatrics, 75(4), (Apr. 1985), 730-736.

Clark, David M., et al., "Hemodynamic Effects of an Irregular Sequence of Ventricular Cycle Lengths During Atrial Fibrillation", JACC, vol. 30, No. 4, (Oct. 1997), 1039-1045.

Cohen, R. J., et al., "Quantitative Model for Ventricular Response During Atrial Fibrillation", IEEE Transactions on Biomedical Engineering, 30, (1983), 769-782.

Duckers, H. J., et al., "Effective use of a novel rate-smoothing algorithm in atrial fibrillation by ventricular pacing", European Heart Journal, 18, (1997), 1951-1955 pgs.

Fahy, G. J., et al., "Pacing Strategies to Prevent Atrial Fibrillation", Atrial Fibrillation, 14(4), (Nov. 1996), 591-596.

Fromer, M., et al., "Algorithm for the Prevention of Ventricular Tachycardia Onset: The Prevent Study", The American Journal of Cardiology, 83 (5B), (Mar. 11, 1999), 450-470 pgs.

Garrigue, S., et al., "Prevention of Atrial Arrhythmias during DDD Pacing by Atrial Overdrive", Pacing and Clinical Electrophysiology, 21(9), (Sep. 1998), 1751-1759.

Greenhut, S., et al., "Effectiveness of a Ventricular Rate Stabilization Algorithm During Atrial Fibrillation in Dogs", Pace Abstract, Abstract No. 60, (1996), 1 pg.

(56) References Cited

OTHER PUBLICATIONS

Guidant, "CONTAK TR CHFD Model 1241", System Guide, Congestive Heart Failure Device, (1999), 1-191.

Heuer, H., et al., "Dynamic Dual-Chamber Overdrive Pacing with an Implantable Pacemaker System: A New Method for Terminating Slow Ventricular Tachycardia", Zeitschrift fur Kardiologie, 75, German Translation by the Ralph McElroy Translation Company, Austin, TX, (1986), 6 pages.

Heuer, H., et al., "Dynamische Zweikammer-Overdrive-Stimulation mit einem implantierbaren Schrittmachersystem als neue Methode zur Beendigung Langsamer ventrikularer Tachykardien", Z Kardiol; 75, Includes English translation (5 pgs.), (1986), 673-675 pgs.

Jenkins, J., et al., "Diagnosis of Atrial Fibrillation Using Electrogram from Chronic Leads: Evaluation of Computer Algorithm", Pacing and Clinical Electrophysiology, 11(5), (1988), 622-631.

Jung, J., et al., "Discrimination of Sinus Rhythm, Atrial Flutter, and Atrial Fibrillation Using Bipolar Endocardial Signals", Journal of Cardiovascular Electrophysiology, 9 (7), (Jul. 1998), 689-695 pgs.

Krig, D. B, et al., "Method and Apparatus for Treating Irregular Ventricular Contractions Such as During Atrial Arrhythmia", U.S. Appl. No. 09/316,515, filed May 21, 1999, 57 pgs.

Lau, C. P., et al., "A new pacing method for rapid regularization and rate control in atrial fibrillation", Am J Cardiol., 65(18), (May 15, 1990), 1198-203.

Lau, Chu-Pak, et al., "Efficacy of Ventricular Rate Stabilization by Right Ventricular Pacing During Atrial Fibrillation", Pacing and Clinical Electrophysiology, 21(3), (Mar. 1998), 542-548.

Lovett, E. G., "Cardiac Pacing System for Prevention of Ventricular Fibrillation and Ventricular Tachycardia Episodes", U.S. Appl. No. 09/569,295, filed May 13, 2000, 30 pgs.

Medtronic, "Insync III Device Model 8042", Device Programming Guide, Insync III Device Model 8042, Vision Programmer Software Model 9981, (2000), 1-260.

Medtronic, "Insync III Device Model 8042", Device Reference Guide, Insync III Device Model 8042, Vision Programmer Software Model 9981, (2002), 1-252.

Mehra, R., et al., "Prevention of Atrial Fibrillation/Flutter by Pacing Techniques", Interventional Electrophysiology, Second Edition, Chapter 34, Futura Publishing Company, Inc., (1996), 521-540 pgs.

Morris, M. M., et al., "Intracardiac Electrogram Transformation: Morphometric Implications for Implantable Devices", Journal of Electrocardiology, 29 Supplement, (1996), 124-129.

Mower, Morton, "Method and Apparatus for Treating Hemodynamic Disfunction", U.S. Patent Office Patent Application Information Retrieval (PAIR) search results for U.S. Appl. No. 10/214,474, filed Aug. 8, 2002, entitled, 3 pgs.

Murgatroyd, F. D., et al., "A New Pacing Algorithm for Overdrive Suppression of Atrial Fibrillation", Pacing and Clinical Electrophysiology, 17(11 Pt. 2), (Nov. 1994, Part), 1966-1973.

Schuller, H., et al., "Far Field R-Wave Sensing—An Old Problem Repeating", Pacing and Clinical Electrophysiology, 19, Part II, NASPE Abstract No. 264, (1996), p. 631.

Seim, G., et al., "Classification of Atrial Flutter and Atrial Fibrillation Using an Atrial Dispersion Index (ADI)", Guidant CRM Therapy Research Peer Review Report Revision 2.0, (Jan. 6, 1999), 27 pgs.

St. Jude Medical, "Atlas + HF Models V-343, V-341", User's Manual, Implantable Cardioverter-Defibrillator, (Sep. 2003), 1-30.

St. Jude Medical, "Epic HF Model V-339", User's Manual, Implantable Cardioverter-Defibrillator, (Jul. 2002), 1-26.

St. Jude Medical, "Model 3510 Programmer with Model 3307 Software", Reference Manual, For Atlas, Atlas+, Epic, Epic+, Photon u and Photon Implantable Cardioverter/Defibrillators, (Sep. 2003), 1-314.

Stephany, G. R., et al., "Real-Time Estimation of Magnitude-Square Coherence for Use in Implantable Devices", IEEE Computers in Cardiology, (1992), 375-378 pgs.

Sutton, R., "Pacing in Atrial Arrhythmias", Pacing and Clinical Electrophysiology, 13(12), (Dec. 1990, Part), 1823-1827.

Sweeney, M. O., et al., "Adverse Effect of Ventricular Pacing on Heart Failure and Atrial Fibrillation Among Patients With Normal Baseline QRS Duration in a Clinical Trial of Pacemaker Therapy for Sinus Node Dysfunction", Circulation, 107(23), (Jun. 17, 2003), 2932-2937.

Swiryn, S., et al., "Detection of Atrial Fibrillation by Pacemakers and Antiarrhythmic Devices", Nonpharmacological Management of Atrial Fibrillation, Chapter 21, Futura Publishing Co, Inc. Armonk, NY, (1997), 309-318 pgs.

Tse, H. F., et al., "Effects of ventricular rate regularization pacing on quality of life and symptoms in patients with atrial fibrillation (Atrial fibrillation symptoms mediated by pacing to mean rates [AF Symptoms study])", Am J Cardiol., 94(7), (Oct. 2004), 938-41.

Wittkampf, F. H.M ., et al., "Rate Stabilization by Right Ventricular Patching in Patients with Atrial Fibrillation", Pace, 9(6)(Part 2), (Nov.-Dec. 1986), 1147-1153.

Wittkampf, Fred H.M., et al., "Effect of Right Ventricular Pacing on Ventricular Rhythm During Atrial Fibrillation", JACC, vol. 11, No. 3, (Mar. 1988), 539-545.

Zhu, D. W, "Electrophysiology, Pacing and Arrhythmia: Pacing Therapy for Atrial Tachyarrhythmias", Clinical Cardiology, 19(9), (1996), 737-742.

"Japanese Application Serial No. 2010-537922, Response filed Jun. 14, 2013 to Non Final Office Action dated Dec. 18, 2012", With English Claims, 7 pgs.

* cited by examiner

SUPRAVENTRICULAR TACHY SENSING VECTOR

CLAIM OF PRIORITY

This application is a continuation of U.S. application Ser. No. 12/277,101, filed Nov. 24, 2008, which claims the benefit under 35 U.S.C. 119(e) of U.S. Provisional Application No. 61/007,635, filed on Dec. 13, 2007, each of which is hereby incorporated by reference in its entirety.

TECHNICAL FIELD

This relates to the field of medical devices, and more specifically to a sensing vector for an implantable device.

BACKGROUND

Pulse generators and leads having electrodes implanted in or about the heart have been used to reverse certain life threatening arrhythmia, or to stimulate contraction of the heart. Electrical energy is applied to the heart via an electrode to return the heart to normal rhythm. Leads are usually positioned on, in, or near the ventricle or the atrium and the lead terminal pins are attached to a pacemaker or defibrillator which is implanted subcutaneously. The pulse generator is configured to utilize the electrodes to receive signals from the heart which can indicate certain cardiac events.

SUMMARY

A system includes a pulse generator including a can electrode and a lead couplable to the pulse generator, the lead including a distal coil electrode and a proximal coil electrode, wherein both of the coil electrodes are electrically uncoupled from the can electrode such that a unipolar sensing vector is provided between at least one of the coil electrodes and the can electrode.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
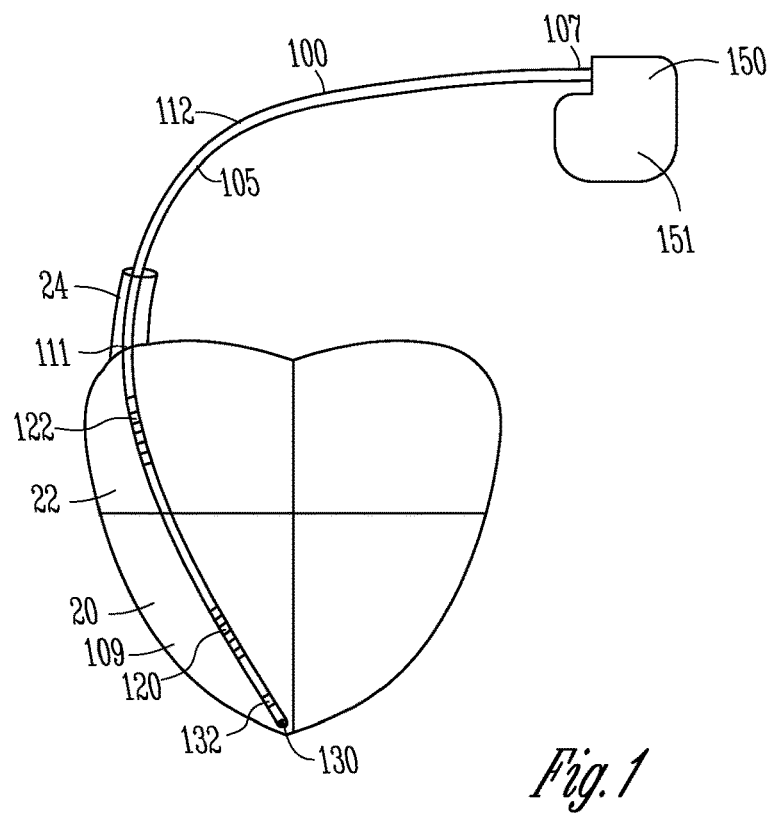
FIG. 1 shows a lead and pulse generator in accordance with one embodiment.

FIG. 1 shows a view of a lead 100 coupled to a pulse generator 150. In one embodiment, lead 100 is adapted to deliver defibrillation shock energy to a heart. Certain embodiments deliver pacing pulses to a heart. Pulse generator 150 can be implanted in a surgically-formed pocket in a patient's chest or other desired location. Pulse generator 150 generally includes electronic components to perform signal analysis, processing, and control. Pulse generator 150 can include a power supply such as a battery, a capacitor, and other components housed in a case or can 151. The device can include microprocessors to provide processing and evaluation to determine and deliver electrical shocks and pulses of different energy levels and timing for ventricular defibrillation, cardioversion, and pacing to a heart in response to cardiac arrhythmia including fibrillation, tachycardia, and bradycardia.

In one embodiment, lead 100 includes a lead body 105 extending from a proximal end 107 to a distal end 109 and having an intermediate portion 111. Lead 100 includes one or more conductors, such as coiled conductors or other conductors, to conduct energy from pulse generator 150 to one or more electrodes, such as a distal defibrillation coil electrode 120 configured to be implanted in right ventricle 20, and a proximal defibrillation coil electrode 122 configured to be implanted in right atrium 22 or superior vena cava 24. The superior vena cava and the right atrium are called the supraventricular portion of the heart. In one embodiment, the lead 100 can include a tip electrode 130 and a distal ring electrode 132 for ventricular sensing and pacing. Some embodiments include one or more proximal ring electrodes for atrial sensing and pacing.

Lead 100 can include lead terminal pins which are attached to pulse generator 150 at a header. The system can include a unipolar system with the housing can 151 acting as an electrode or a bipolar system with a pulse between two electrodes 120, 122, or electrodes 130, 132.

The present system is directed to providing a supraventricular tachycardia sensing vector. The present system provides a technique to better distinguish supraventricular tachycardia (SVT) from ventricular tachycardia (VT). For example, in a past approach, the proximal coil 122 was electrically coupled to can electrode 151 and tachycardia sensing was performed using the distal coil 120 to both the can 151 plus the proximal coil 122. However, this configuration results in difficulties in distinguishing between SVT and VT.

In one embodiment, the present system electrically isolates the can electrode 151 from proximal coil electrode 122 and from the distal coil electrode 120 to provide a supraventricular tachy sensing vector. For example, coil electrode 122 can be electrically isolated from the can electrode 151 and a unipolar sensing vector can be from the proximal coil electrode 122 to the can electrode 151. In one embodiment, a unipolar sensing vector can be from the distal coil 120 to the can electrode 151. In one embodiment, a sensing vector can be from distal coil 120 to proximal electrode 122. These configurations are useful for distinguishing between SVT and VT.

In other embodiments, the present system uncouples the proximal electrode 122 from the can 151 and provides sensing utilizing one or more of electrodes 130, 132.

The term sensing vector is described herein by the location of the two electrodes used by a sensing channel within the pulse generator. The sensing channel uses the electrical signal that exists between the two electrodes to sense cardiac activity. Different sense vectors will present different aspects of the cardiac signal to the sensing channel. In the present embodiments, the sense vectors have improved performance for sensing SVT because these vectors produce a larger SVT to VT signal ratio than in the past.

Thus in various examples, both of the coil electrodes 120, 122 are electrically uncoupled from the can electrode 151 such that a unipolar sensing vector is provided between at least one of the coil electrodes and the can electrode 151. For example, the sensing vector can be provided between the distal electrode 120 and the can electrode 151, or the sensing vector can be provided between the proximal electrode 122 and the can electrode 151. In another example a second sensing vector can be provided between the distal coil electrode 120 and the proximal coil electrode 122.

In another example, the pulse generator can be configured such that the unipolar sensing vector can alternate between the distal coil electrode 120 and the can electrode 151 and the proximal electrode 122 and the can electrode 151. In one embodiment, the pulse generator is configured such that a first unipolar sensing vector between the distal coil electrode 120 and the can electrode 151 and a second unipolar sensing vector between the proximal electrode 122 and the can electrode 151 occur simultaneously.

The pulse generator can be configured to distinguish between VT and SVT using the unipolar sensing vectors discussed above. For example, one technique to distinguish between VT and SVT is to use a template of the correlation between shock vector electrograms and RV rate vector electrograms during normal sinus rhythm. When an arrhythmia is detected, the template is compared to the on-going rhythm; if the rhythm matches the existing template, then it is believed that the origin of the rhythm is supraventricular and the device withholds therapy—the assumption being that a supraventricular rhythm follows the same conduction pathway as normal sinus rhythm, and thus the correlation of the two vectors during SVT would match the normal sinus rhythm template, and therapy can be delivered.

However, if the correlation of the vectors during the rhythm does not match the template, then it is assumed that the rhythm is VT (i.e. the rhythm is not using the normal conduction pathway).

Further embodiments can use a different template created from the new vectors described herein. This new template would provide more power to discriminate problem cases using the template described above—and thus more information from the combination of more vectors would yield more discrimination power.

In one embodiment, electrode 122 is disposed along the lead such that the electrode 122 is configured to be located in the right atrium 22 or superior vena cava 24 after implantation.

Figure 2:
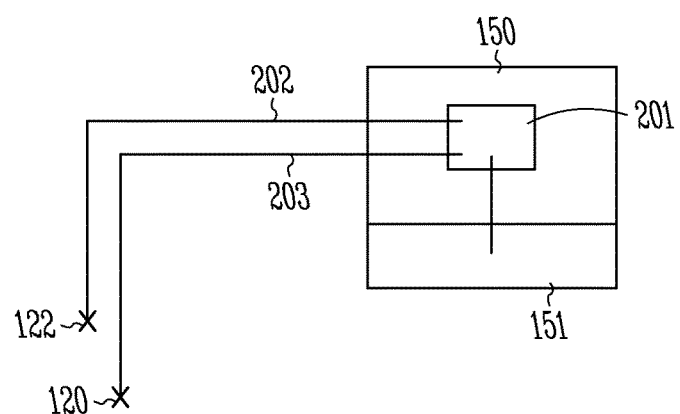
FIG. 2 shows a schematic representation of a lead and pulse generator in accordance with one embodiment.

FIG. 2 shows a schematic representation of portions of the system described above, in accordance with one embodiment. The lead includes a first conductor 202 coupled between the proximal coil electrode 122 and electronics 201 within the pulse generator 150. The lead also includes a second conductor 203 coupled between distal coil electrode 120 and electronics 201. The can electrode 151 is also coupled to the electronics 201. Electronics 201 includes electrically pathways which provide that the electrodes 122, and 120 are electrically insulated from the can electrode 151. As discussed, the electronics 201 can be configured to allow the various connections to be uncoupled or coupled as desired.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method comprising:
    providing a lead and an associated pulse generator, the pulse generator including a can electrode, the lead including a proximal coil electrode which is electrically isolated from the can electrode, and the lead including a distal coil electrode which is electrically isolated from the can electrode;
    sensing heart signals using a first unipolar sensing vector between the distal coil electrode and the can electrode and a second unipolar sensing vector between the proximal coil electrode and the can electrode.

2. The method of claim 1, wherein sensing heart signals includes the pulse generator differentiating between SVT signals and VT signals.

3. The method of claim 2, wherein differentiating between SVT signals and VT signals includes using a template of a correlation between shock vector electrograms and RV rate vector electrograms during normal sinus rhythm.

4. The method of claim 3, including detecting an arrhythmia from a heart signal, wherein when the arrhythmia is detected, the template is compared to an on-going rhythm, and when the on-going rhythm matches the existing template, then the pulse generator withholds therapy.

5. The method of claim 1, wherein the lead further includes one or more distal pacing and/or sensing electrodes.

6. The method of claim 1, wherein a third sensing vector is provided between the distal coil electrode and the proximal coil electrode.

7. The method of claim 1, wherein the pulse generator is configured such that a sensed unipolar sensing vector can alternate between the first unipolar sensing vector between the distal coil electrode and the can electrode and the second unipolar sensing vector between the proximal electrode and the can electrode.

8. The method of claim 1, wherein the pulse generator is configured such that a first unipolar sensing vector between the distal coil electrode and the can electrode and a second unipolar sensing vector between the proximal electrode and the can electrode occur simultaneously.

* * * * *